United States Patent [19]

Johnson

[11] 4,237,061

[45] Dec. 2, 1980

[54] ORGANOMETALLIC INTERCALATES

[75] Inventor: Jack W. Johnson, Fanwood, N.J.

[73] Assignee: Exxon Research & Engineering Co., Florham Park, N.J.

[21] Appl. No.: 191

[22] Filed: Jan. 2, 1979

[51] Int. Cl.$^2$ .......................... C07F 7/00; C07F 15/06
[52] U.S. Cl. ................................ 260/429.3; 250/272; 260/429 R; 260/429 AR; 260/429 CY; 260/429 L; 260/429.1; 260/429.2; 260/429.5; 260/429.7; 260/439 R; 260/439 CY
[58] Field of Search ................. 260/429 CY, 439 CY, 260/429.3, 429.5, 435, 429.7, 429 R, 429 AR, 429.2

[56] References Cited

U.S. PATENT DOCUMENTS

| | | | |
|---|---|---|---|
| 2,953,586 | 9/1960 | Hafner et al. | 260/429 AR |
| 3,673,015 | 6/1972 | Sollott et al. | 260/439 CY |
| 3,688,109 | 8/1972 | Gamble | 260/429 R X |
| 3,980,684 | 9/1976 | Dines | 260/429 CY |
| 4,024,170 | 5/1977 | Atwood | 260/429 AR X |
| 4,094,893 | 6/1978 | Dines | 260/429 R |
| 4,119,655 | 10/1978 | Hulme | 260/429.3 X |

OTHER PUBLICATIONS

Alberti, Accounts of Chemical Research 11, 163-170 (1978).
Alberti et al., J. Inorg. Nucl. Chem., vol. 40, pp. 1113-1117 (1978).
Weigel et al., J. of the Less-Common Metals, vol. 44, 99-123, 125-136, 133-136 (1976).

*Primary Examiner*—Helen M. S. Sneed
*Attorney, Agent, or Firm*—David W. Collins; James H. Takemoto

[57] ABSTRACT

A new group of materials comprises intercalates of organometallic compounds in layered structures of water-insoluble salts comprised of a tetravalent metal cation and an acid phosphate, arsenate or vanadate anion. Related materials comprise intercalates of organometallic compounds in layered structures of uranyl and transuranyl phosphates, arsenates and vanadates. Intercalation hosts are represented either by the formula $M(H_{1-y}A_yXO_4)_2 \cdot nH_2O$ or by the formula $H_{1-y}A_yTO_2XO_4 \cdot nH_2O$, where M is at least one tetravalent cation selected from the group consisting of zirconium, titanium, hafnium, cerium, thorium, tin, lead and germanium, A is at least one monovalent cation selected from the group consisting of lithium, sodium, potassium, rubidium, cesium, ammonium and substituted ammonium, X is at least one element selected from the group consisting of phosphorus, arsenic and vanadium, T is at least one element selected from the group consisting of uranium and transuranic elements, "y" ranges from 0 to 1 and "n" ranges from 0 to 6. Intercalated guests comprise an organometallic cation with a transition metal to which from 2 to 6 ligands are bonded.

13 Claims, 2 Drawing Figures

ORGANOMETALLIC INTERCALATES

BACKGROUND OF THE INVENTION

1. Field of the Invention

The invention is directed to organometallic intercalation compounds.

2. Description of the Prior Art

Organometallic intercalation compounds are disclosed in U.S. Pat. No. 3,980,684. The disclosed intercalation compounds are layered structures of metal dichalcogenides and metallocenes. The materials are disclosed as suitable for diffracting soft X-rays with wavelengths as long as about 20Å.

SUMMARY OF THE INVENTION

In accordance with the invention, a novel composition of matter comprises an intercalation host and an intercalated guest, the host being a water-insoluble salt comprised of a tetravalent metal cation and an acid phosphate, arsenate or vanadate anion and having a layered structure and the guest being an organometallic cation stable to water at ambient temperatures. The host is represented by the formula $M(H_{1-y}A_yXO_4)_2 \cdot nH_2O$, where M is at least one tetravalent metal cation selected from the group consisting of zirconium, titanium, hafnium, cerium, thorium, tin, lead and germanium, A is at least one monovalent cation selected from the group consisting of lithium, sodium, potassium, rubidium, cesium, ammonium ($NH_4^+$) and substituted ammonium of the formula $RR'R''R'''N^+$, where R, R', R'' and R''' are selected from the group consisting of hydrogen and hydrocarbon radical, X is at least one element selected from the group consisting of phosphorus, arsenic and vanadium, "y" ranges from 0 to 1 and "n" ranges from 0 to 6. The guest is an organometallic cation comprised of a transition metal selected from Groups IB to VIIB and VIII, Rows 4, 5 and 6 of the Periodic Table of Elements, and has from 2 to 6 ligands bonded thereto.

Also in accordance with the invention, a novel composition of matter comprises an intercalation host and an intercalated guest, the host being a layered phosphate of a different layered structural type and stoichiometry, represented by $H_{1-y}A_yTO_2XO_4 \cdot nH_2O$, where T is at least one element selected from the group consisting of uranium and transuranic elements and A, X, "y", "n" and the intercalated guest are as given above.

An ion exchange technique is used to form the intercalation compounds in which an organometallic cation is intercalated. On the other hand, the intercalation compounds of the invention may also be prepared utilizing neutral organometallic compounds by direct reaction technique.

DETAILED DESCRIPTION OF THE INVENTION

Figure 1:
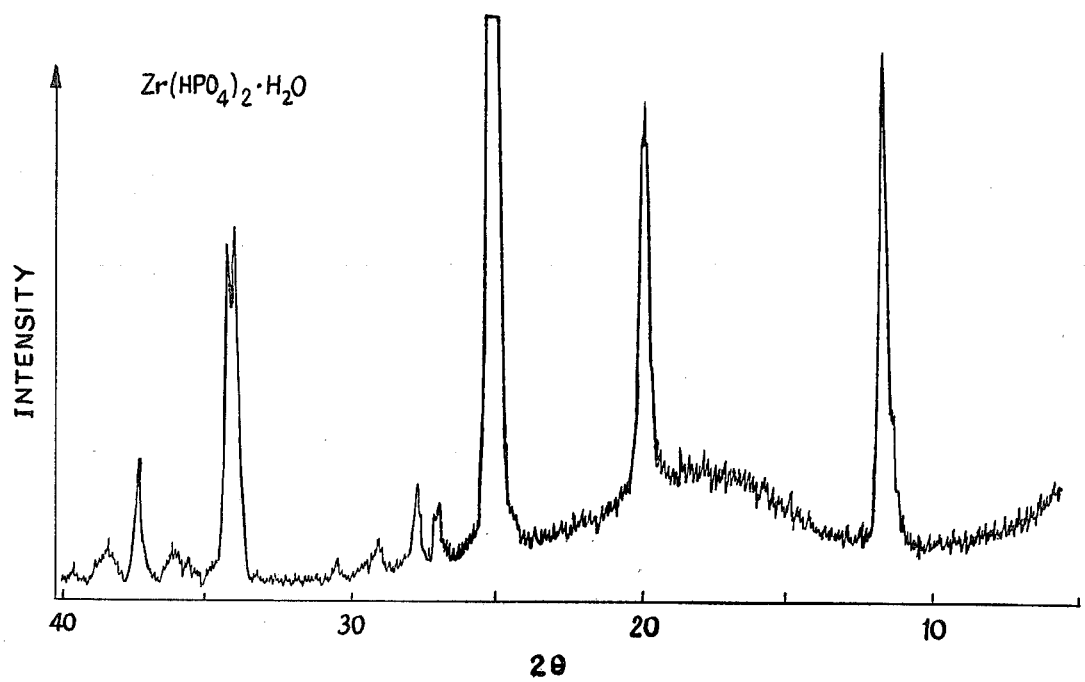
FIG. 1 is an X-ray diffraction profile of $Zr(HPO_4)_2 \cdot H_2O$, prior to intercalation.

Intercalation compounds comprise an intercalation host and an intercalated guest. The novel compositions of matter of the invention include as intercalation hosts any water-insoluble salt comprised of a tetravalent metal cation and an acid phosphate, arsenate or vanadate anion and having a layered structure. Protons of the phosphate, arsenate or banadate group may be partially or wholly replaced by monovalent cations. The intercalation host of the invention is represented by the formula $M(H_{1-y}A_yXO_4)_2 \cdot nH_2O$, where M is at least one tetravalent metal cation selected from the group consisting of zirconium, titanium, hafnium, cerium, thorium, tin, lead and germanium, A is at least one monovalent cation selected from the group consisting of lithium, sodium, potassium, rubidium, cesium, ammonium ($NH_4^+$) and substituted ammonium of the formula $RR'R''R'''N^+$, where R, R', R'' and R''' are selected from the group consisting of hydrogen and hydrocarbon radical, X is at least one element selected from the group consisting of phosphorus, arsenic and vanadium, "y" ranges from 0 to 1 and "n" ranges from 0 to 6. The preparation of these salts is well-known and forms no part of this invention; see, e.g., Volume 11, Accounts of Chemical Research, pages 163-170 (1978). The planar structure of the host compound comprises trigonal arrays of tetravalent M cations octahedrally coordinated by triply bridging $H_{1-y}A_yXO_4^=$ groups. The particular structure of the layered compound depends on the guest cations and the degree of solvation between layers.

Preferably, "y" is 0; such compounds have the formula $M(HXO_4)_2 \cdot nH_2O$. Exemplary of a salt of this type is zirconium phosphate, $Zr(HPO_2)_4 \cdot nH_2O$.

A second class of intercalation hosts are layered phosphates, arsenates and vanadates given by the formula $H_{1-y}A_yTO_2XO_4 \cdot nH_2O$, where T is at least one element selected from the group consisting of uranium and transuranic elements. Examples of transuranic elements include neptunium and americium. The preparation of these salts is well-known and forms no part of this invention; see, e.g., Volume 44, Journal of the Less Common Metals, pp 99-123, 125-132, 133-136 (1976). A, X, "y" and "n" are as given above. Uranium compounds are comparatively stable and are thus preferred. The planar structure comprises zigzag sheets of close-packed $UO_2^{++}$ and $XO_4^{3-}$ groups. Again, the particular structure of the layered compound depends on the guest cations and the degree of solvation between layers.

The intercalated guest is an organometallic cation comprising a transition metal to which from 2 to 6 ligands are bonded. The transition metal is selected from the group consisting of elements in Groups IB to VIIB and VIII, Rows 4, 5 and 6 of the Periodic Table of Elements. The molar ratio of intercalated guest to intercalation host is about 0.5 or less.

Briefly, there are two ways to prepare the intercalation compounds of the invention. The first is an ion exchange technique and the second is a direct mixing technique. Both techniques are discussed in further detail below.

Using the ion exchange technique, an organometallic cation exchanges for $H^+$ and/or $A^+$ cation or cations. The organometallic cation is one which is stable to water at ambient temperatures. The ligands bonded to the transition metal may be the same or different. The ligands are selected from the group consisting of unsaturated hydrocarbons, organophosphites, organophosphines, organoarsines, organic isocyanides, carbon monoxide, nitric oxide, hydride, halide, pseudohalide, alkyl and aryl. Examples of unsaturated hydrocarbons include simple alkenes, polyenes, allyl and polyenyl groups such as ethylene, allyl, butadiene, pentadienyl, cyclopentadienyl, benzene, cycloheptadienyl and the like and their substituted derivatives. Examples of organophosphites, organophosphines and organoarsines include $P(C_6H_5)_3$, $As(CH_3)_3$, $As(CH_3)_2C_6H_5$, $PHK(C_6H_5)_2$, $P(OC_2H_5)_3$, $P(OCH_3)(C_6H_5)_2$ and the like. Organoisocyanides include $CH_3NC$, $C_6H_5NC$ and the like. Halides and pseudohalides include Cl, Br, I, CN, SCN, $N_3$ and the like. Alkyl and aryl groups include $CH_3$, $C_6H_5$, $CH_2C(CH_3)_3$ and the like.

Examples of organometallic cations suitable for preparing the intercalated compounds of the invention include $[Co(C_5H_5)_2]^+$, $[Fe(C_5H_5)(C_6H_5CH_3)]^+$, $[Co(CH_3NC)_5]^+$, $[Rh(C_6(CH_3)_6)(C_2H_4)_2]^+$, $[Cr(C_6H_6)_2]^+$, $[NiC_3H_5(P(OCH_3)_3)_3]^+$ and $[Rh[(C_6H_5)_2PCH_2CH_2P(C_6H_5)_2]_2]^+$. In general, any anion, such as $OH^-$, $PF_6^-$, halide, and the like, may be associated with the organometallic cation except as noted below.

In the ion exchange reaction, a solid layered compound containing exchangeable cations ($H^+$ and/or $A^+$) is mixed with a solution comprising an organometallic cation dissolved in a solvent. The following reaction is considered typical of the ion exchange reactions:

$Zr(HPO_4)_2 + xCo(C_5H_5)_2^+ \rightarrow Zr(HPO_4)_{2-x}(PO_4)_x \cdot (Co(C_5H_5)_2)_x + xH^+$ where "x" is about 0.5 or less. Solvents useful in the practice of the ion exchange reaction are polar and capable of dissolving the organometallic salt. Such solvents include the following materials: water, methanol, ethanol, dimethylsulfoxide, dimethylformamide, tetrahydrofuran, acetonitrile and the like and mixtures thereof.

The temperature of the reaction may range from ambient to just below the decomposition temperature of the organometallic compound. Reaction time typically takes from a few hours to several weeks, depending on the particular reactants.

Although all combinations of organometallic cations and intercalation hosts may be expected to form the novel intercalation compounds of the invention, some particular combinations may not react as completely as others. For example, the crystalline modification of the host compound can affect the facility of the intercalation reaction. As an example, the gamma-phase of $Zr(HPO_4)_2 \cdot 2H_2O$ reacts well with $Co(C_5H_5)_2PF_6$ to form intercalated cobaltocenium cations between the layers of the zirconium phosphate lattice. On the other hand, under similar conditions, the alpha-phase of $Zr(HPO_4)_2 \cdot H_2O$ evidences little reaction with the organometallic cation. However, changing the anion from $PF_6^-$ to $OH^-$ leads to intercalation of the cobaltocenium cation. Thus, in many instances in which the ion exchange reaction does not readily proceed to completion, altering the anion may effect the desired intercalation.

By the direct reaction technique, neutral organometallic compounds are employed that (a) have a low enough ionization potential that they reduce $H^{30}$ and (b) have stable corresponding cations. Examples of neutral organometallic compounds are given by the formula $M'(C_mH_{m-q}R_q)_2$, where M' is at least one transition metal from Groups IB to VIIB and VIII, Rows 4, 5, and 6 of the Periodic Table, R is an organic radical which is the same or different and is selected from the group consisting of $C_1$-$C_2$ linear and $C_3C_4$-$C_{12}$ branched hydrocarbyls, $C_3$-$C_{12}$ cyclic alkyls, $C_2$-$C_{12}$ alkenyls, $C_2$-$C_{12}$ alkynyls, $C_1$-$C_{12}$ alkoxy, $C_6$-$C_{18}$ aryloxy and $C_6$-$C_{18}$ aryl, "m" is an integer from 5 to 7 and "q" is an integer from 0 to "m". For "m" equal to 5, organometallic cations having the requisite ionization potential are readily formed with chromium and cobalt and accordingly, these transition elements are preferred. Examples of neutral organometallic compounds suitable in the practice of the invention include $Co(C_5H_5)_2$, $Cr(C_6H_6)_2$ and $Mo(C_6H_5CH_3)_2$.

An example of the direct reaction of a neutral organometallic compound having a suitably low ionization potential, as discussed above, with a solid layered compound containing reducible groups ($H^+$) in an inert solvent is given as follows:

$Zr(HPO_4)_2 + xCo(C_5H_5)_2 \rightarrow Zr(HPO_4)_{2-x}(PO_4)_x \cdot (Co(C_5H_5)_2)_x + x/2 H_2$ where "x" is about 0.5 or less. The inert solvent used may be any solvent that is not reduced by the organometallic compound. Examples of suitable solvents include toluene, benzene and hexane.

The reaction is carried out at elevated temperatures; about 80° to 120° C. is suitable. Reaction time typically takes from a few days to several weeks, depending on the particular reactants.

The reaction is preferably carried out in the absence of oxygen in order to avoid adverse side reactions. Inert atmospheres such as helium, argon and nitrogen or partial vacuum are suitable.

The new compositions of matter are easily characterized as layered compounds by X-ray diffraction. The stoichiometry is established by elemental analysis. These new compositions of matter are useful as catalysts or catalyst precursors, diffraction gratings and cation exchange materials.

EXAMPLES

Example 1—Ion Exchange Reaction

In 30 ml of 50% methanol/water was dissolved 0.21 g of $Co(C_5H_5)_2PF_6$. To the solution was added 0.20 g of gamma-$Zr(HPO_4)_2 \cdot 2H_2O$, and the resulting suspension was stirred at room temperature for two days. A yellow solid formed and was filtered and dried in vacuo. X-ray diffraction and elemental analysis indicated the incorporation of cobaltocenium cations between the layers of the zirconium phosphate lattice.

Example 2—Direct Reaction

Figure 2:
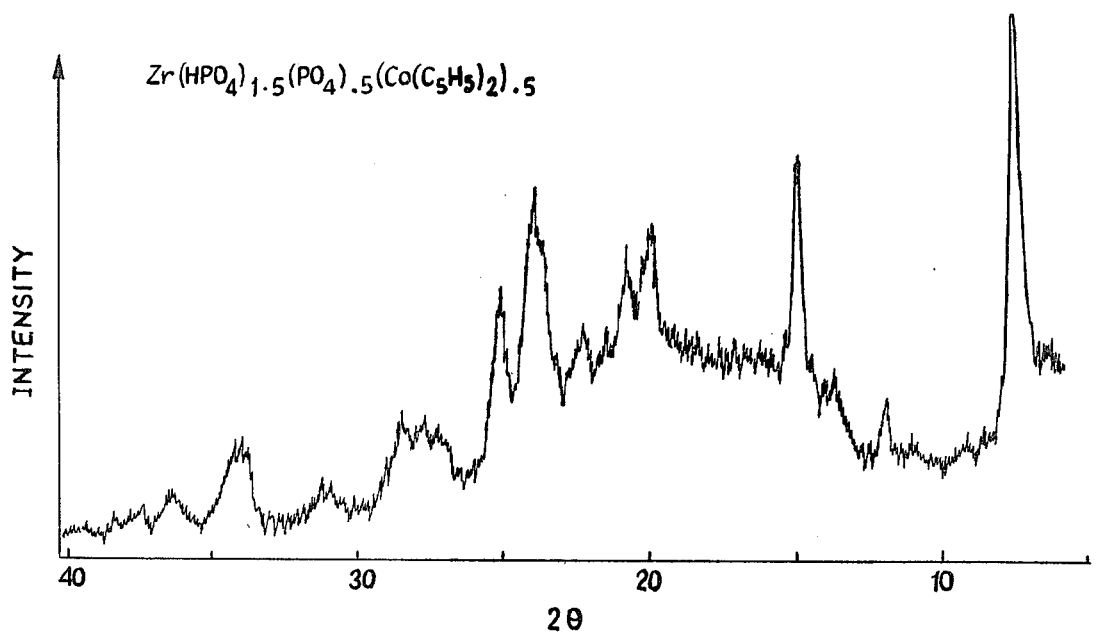
FIG. 2 is an X-ray diffraction profile of intercalated $Zr(HPO_4)_{1.5}(PO_4)_{0.5}(Co(C_5H_5)_2)_{0.5}$.

A mixture of 0.236 g of alpha-$Zr(HPO_4)_2 \cdot H_2O$, 0.074 g of $Co(C_5H_5)_2$ and 2.5 ml of dry toluene were placed in a Carius tube in an inert atmosphere of helium. The tube was cooled, evacuated and sealed with a torch. After heating at 110°–120° C. for eleven days, the supernatant was clear, demonstrating the complete reaction of the cobaltocene. The green-yellow solid was separated by filtration and dried in an inert atmosphere of helium to yield 0.315 g of product, $Zr(HPO_4)_{1.5}(PO_4)_{0.5} \cdot (Co(C_5H_5)_2)_{0.5}$, which was characterized by X-ray diffraction and elemental analysis. The X-ray diffraction profiles of the starting material and the final product are shown in FIGS. 1 and 2, respectively. The position of the two low angle peaks indicate that the interlayer distance in the product has expanded to 12.2 Å from the 7.6 Å interlayer distance in the starting material.

Example 3

A mixture of 0.612 g of $HUO_2PO_4 \cdot 4H_2O$, 0.132 g of $Co(C_5H_5)_2$ and 2.5 ml of toluene were placed in a Carius tube in an inert atmosphere of helium. The tube was cooled, evacuated and sealed with a torch. After heating at 110° C. for four days, the supernatant was clear, illustrating complete reaction of the cobaltocene. The yellow solid product (0.677 g) was separated by filtration. X-ray powder diffraction revealed that the product was a new phase with an interlayer distance of 12.6 Å, an expansion of 4.1 Å relative to the starting material. This, together with the weight gain, indicated the incorporation of cobaltocene into the interlayer space with a concurrent expulsion of $H_2O$.

What is claimed is:

1. A composition of matter comprising an intercalation host and an intercalated guest, said host represented by $M(H_{1-y}A_yXO_4)_2 \cdot nH_2O$, where M is at least one tetravalent metal cation selected from the group consisting of zirconium, titanium, hafnium, cerium, thorium, tin, lead and germanium, A is at least one monovalent cation selected from the group consisting of lithium, sodium, potassium, rubidium, cesium, ammonium and substituted ammonium of the formula $RR'R''R'''N^+$, where R, R', R'', and R''' are selected from the group consisting of hydrogen and hydrocarbon radicals, X is at least one element selected from the group consisting of phosphorus, arsenic and vanadium, "y" ranges from 0 to 1 and "n" ranges from 0 to 6 and said guest is an organometallic cation comprised of a transition metal selected from Groups IB to VIIB and VIII, Rows 4, 5 and 6 of the Periodic Table of Elements and from 2 to 6 ligands bonded thereto, said ligands being independently selected from the group consisting of unsaturated hydrocarbons, organophosphites, organophosphines, organoarsines, organic isocyanides, carbon monoxide, nitric oxide, hydride, halide, pseudohalide, alkyl and aryl.

2. The composition of claim 1 in which said composition of matter is formed by ion exchange reaction with said host and an organometallic cation which is stable to water at ambient temperatures.

3. The composition of claim 1 in which said organometallic cation is selected from the group consisting of $[Co(C_5H_5)_2]^+$, $[Fe(C_5H_5)(C_6H_5CH_3)]^+$, $[Co(CH_3NC)_5]^+$, $[Rh(C_6(CH_3)_6)(C_2H_4)_2]^+$, $[Cr(C_6H_6)_2]^+$, $[NiC_3H_5(P(OCH_3)_3)_3]^+$ and $[Rh[(C_6H_5)_2PCH_2CH_2[(C_6H_5)_2]_2]^+$.

4. The composition of claim 3 in which said organometallic cation is $[Co(C_5H_5)_2]^+$.

5. The composition of claim 1 in which said composition of matter is formed by direct reaction with said host and a neutral organometallic compound having (a) a low enough ionization potential that it reduces $H^+$ and (b) a stable corresponding cation.

6. The composition of claim 5 in which said neutral organometallic compound is represented by the formula $M'(C_mH_{m-q}R_q)_2$, where M' is at least one transition metal selected from Groups IB to VIIB and VIII, Rows 4, 5 and 6 of the Periodic Table, R is selected from the group consisting of $C_1$-$C_2$ linear and $C_3$-$C_{12}$ linear and branched hydrocarbyls, $C_3$-$C_{12}$ cyclic alkyls, $C_2$-$C_{12}$ alkenyls, $C_2$-$C_{12}$ alkynyls, $C_1$-$C_{12}$ alkoxy, $C_6$-$C_{18}$ aryloxy and $C_6$-$C_{18}$ aryl, "m" is an integer from 5 to 7 and "q" is an integer from 0 to "m".

7. The composition of claim 6 in which "m" is 5.

8. The composition of claim 7 in which M' is at least one of chromium and cobalt.

9. The composition of claim 6 in which said neutral organometallic compound is selected from the group consisting of $Co(C_5H_5)_2$, $Cr(C_6H_6)_2$ and $Mo(C_6H_5CH_3)_2$.

10. The composition of claim 9 in which said neutral organometallic compound is $Co(C_5H_5)_2$.

11. The composition of claim 1 in which the molar ratio of intercalated guest to intercalation host is about 0.5 or less.

12. The composition of claim 1 in which "y" is 0.

13. The composition of claim 12 in which said intercalation host consists essentially of $Zr(HPO_4)_2 \cdot nH_2O$.

* * * * *